US012005201B2

(12) United States Patent
Walish et al.

(10) Patent No.: US 12,005,201 B2
(45) Date of Patent: Jun. 11, 2024

(54) PUNCTURE VISUALIZATION DEVICE AND METHOD (71) Applicant: GYRUS ACMI, INC., Westborough, MA (US)

(72) Inventors: Judy L. Walish, Boston, MA (US); Bruce W. Flight, Melrose, MA (US)

(73) Assignee: Gyrus ACMI, Inc., Westborough, MA (US)

(*) Notice: Subject to any disclaimer, the term of this patent is extended or adjusted under 35 U.S.C. 154(b) by 67 days.

(21) Appl. No.: 17/301,235

(22) Filed: Mar. 30, 2021

(65) Prior Publication Data
US 2021/0299407 A1 Sep. 30, 2021

Related U.S. Application Data (60) Provisional application No. 63/002,733, filed on Mar. 31, 2020.

(51) Int. Cl.
A61M 25/01 (2006.01)
A61M 25/00 (2006.01)
(Continued)

(52) U.S. Cl.
CPC .... A61M 25/0138 (2013.01); A61M 25/0097 (2013.01); A61M 25/0625 (2013.01);
(Continued)

(58) Field of Classification Search
CPC .......... A61M 25/0138; A61M 25/0097; A61M 25/0625; A61M 25/09; A61M 2025/0166;
(Continued)

(56) References Cited

U.S. PATENT DOCUMENTS 6,149,660 A * 11/2000 Laufer ............... A61B 17/0684
606/139
8,016,814 B2 9/2011 Blakstvedt et al.
(Continued)

FOREIGN PATENT DOCUMENTS

WO 2021202558 10/2021

OTHER PUBLICATIONS

"International Application Serial No. PCT US2021 024923, Invitation to Pay Additional Fees dated Jun. 22, 2021", 2 pgs.
(Continued)

Primary Examiner — Brandy S Lee
Assistant Examiner — Phoebe Anne Staton
(74) Attorney, Agent, or Firm — Schwegman Lundberg & Woessner, P.A.

(57) ABSTRACT

A puncture visualization device can include a guidewire having a proximal section, a distal section, and a distal tip. The device can include a needle having a needle lumen configured to receive the guidewire. The device can include a lock, and the lock can engage with the guidewire. For instance, engagement of the lock with the guidewire can inhibit relative motion between the guidewire and the needle. The device can include an optical sensor, for example located at the distal tip of the guidewire. The optical sensor can be locked into a position, for instance by the lock.
(Continued)

In an example, the device provides a distal field of view from a location within the needle and near a distal end of the needle for visualization to facilitate puncturing a target with the distal end of the needle.

15 Claims, 6 Drawing Sheets

(51) Int. Cl.
  *A61M 25/06* (2006.01)
  *A61M 25/09* (2006.01)
  *A61B 90/00* (2016.01)
(52) U.S. Cl.
  CPC ..... *A61M 25/09* (2013.01); *A61B 2090/3614* (2016.02); *A61M 2025/0166* (2013.01); *A61M 2025/09125* (2013.01); *A61M 2205/3306* (2013.01); *A61M 2205/332* (2013.01); *A61M 2205/3368* (2013.01); *A61M 2205/583* (2013.01); *A61M 2205/587* (2013.01)
(58) Field of Classification Search
  CPC .... A61M 2205/3306; A61M 2205/332; A61M 2205/3368; A61M 2205/583; A61M 2205/587; A61M 2025/09125; A61M 25/065; A61M 25/01; A61M 25/0169; A61M 39/1011; A61B 17/3421; A61B 1/01; A61B 17/3403; A61B 2017/22042; A61B 2090/3614; A61B 17/3478; A61B 2017/347; A61B 2017/22049

See application file for complete search history.

(56) References Cited

U.S. PATENT DOCUMENTS

| | | | |
|---|---|---|---|
| 9,028,428 B2 | 5/2015 | Maki | |
| 2007/0083132 A1* | 4/2007 | Sharrow | A61M 25/0012 600/431 |
| 2009/0227952 A1* | 9/2009 | Blakstvedt | A61B 5/0084 604/117 |
| 2012/0130230 A1 | 5/2012 | Eichler et al. | |
| 2012/0283640 A1* | 11/2012 | Anderson | A61M 25/09 604/164.1 |
| 2014/0100552 A1* | 4/2014 | Gallacher | A61M 39/20 604/528 |
| 2016/0015945 A1 | 1/2016 | Warring et al. | |

OTHER PUBLICATIONS

"International Application Serial No. PCT US2021 024923, International Search Report dated Aug. 18, 2021", 4 pgs.
"International Application Serial No. PCT US2021 024923, Written Opinion dated Aug. 18, 2021", 8 pgs.
"International Application Serial No. PCT/US2021/024923, International Preliminary Report on Patentability dated Oct. 13, 2022", 10 pgs.

* cited by examiner

PUNCTURE VISUALIZATION DEVICE AND METHOD

CROSS-REFERENCE TO PRIORITY APPLICATION

This application claims the benefit of priority to U.S. Provisional Patent Application No. 63/002,733 filed Mar. 31, 2020, the contents of which are incorporated by reference herein.

TECHNICAL FIELD

This document pertains generally, but not by way of limitation, to medical instruments, for example a guidewire, needle, or the like.

BACKGROUND

A needle can be used puncture tissue anatomy (e.g., skin, muscle, fat, organs, or the like) of a patient during a medical procedure. External medical imaging (e.g., fluoroscopy, x-ray, or the like) can facilitate guiding the needle to a target (e.g., a calyx of kidney, or the like). The needle can be used to puncture tissue along a path toward the target, for example to provide access to the anatomy and to locate a guidewire in the anatomy of the patient.

SUMMARY

The present inventors have recognized, among other things, that a problem to be solved can include guiding a needle toward a target, for instance during a percutaneous puncturing procedure. In some instances, a size of the needle can be large (e.g., over a centimeter in diameter) and opportunities to place or steer the needle can be limited because of the size of the needle. In some approaches, more than one puncture with the needle can be needed, for instance because the needle was guided to a location away from the target. For example, the target can include a first calyx of a kidney, and the needle can puncture and guide the needle to a second calyx of the kidney.

This document explains an approach that can help provide a solution to this problem, such as by providing a puncture visualization device, such as can be located on-board (e.g., on an exterior surface of or preferably within) the needle. For example, the puncture visualization device can provide a distal field of view from a location within the needle, such as from within the needle and at or near a distal end of the needle. The distal field of view, e.g., looking axially out from within the needle, can provide visualization that can help facilitate puncturing a path toward the target with a distal end of the needle.

For instance, the present visualization looking axially out from within the needle can help identify a position of the distal end of the needle within the anatomy. For example, the present visualization from within the needle can help facilitate identifying anatomical structure to determine a location of the needle (e.g., identifying if the needle is in a fat layer, or an organ). Such visualization information, in turn, can facilitate guiding the distal end of the needle toward the target (e.g., anatomy of a patient, for instance a kidney) and puncturing the target or a path toward the target with the distal end of the needle. Accordingly, the puncture visualization device can help enhance guidance of the needle to the target, and can help avoid or minimize a need for repeated punctures.

The present visualization can facilitate navigation along a puncture direction of the needle (e.g., by providing an axial view along a length axis of the needle). For example, external fluoroscopy can facilitate navigation from a perspective that is orthogonal or lateral to the length axis of the needle (or orthogonal or lateral to the axial distally forward-looking perspective provided by the puncture visualization device). Thus, the puncture visualization device can be used to augment fluoroscopy (or vice-versa) such as to help improve the accuracy, precision, or the like of guiding the needle toward the target. Therefore, the additional axial information provided by the puncture visualization device can help avoid or minimize additional punctures that can otherwise be needed to reach the target, for example additional punctures due to errant guidance of the needle (e.g., to a location other than the location of the target). The puncture visualization device can additionally or alternatively be used to help reduce use of fluoroscopy, and accordingly limit exposure of a patient (or a healthcare provider) to radiation as a result of the use of fluoroscopy.

The puncture visualization device can include a guidewire such as having a proximal section, a distal section, and a distal tip. The device can include a needle having a needle lumen configured to receive the guidewire. The device can include a lock, such as can engage with the guidewire. Engagement of the lock with the guidewire can inhibit relative motion between the guidewire and the needle. The device can include an optical sensor, for example located at the distal tip of the guidewire. The optical sensor can be locked into a position (e.g., within the needle lumen), such as with the lock. The puncture visualization device can provide a distal field of view such as from a location within the needle and near a distal end of the needle. The distal field of view can provide visualization (e.g., to a healthcare provider, or the like) to facilitate puncturing toward a target with the distal end of the needle, such as by communicating a visualization signal from the optical sensor to an external visualization display or image signal processing device such as can be analyzed, viewed, observed, or the like by the user during the procedure.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1:
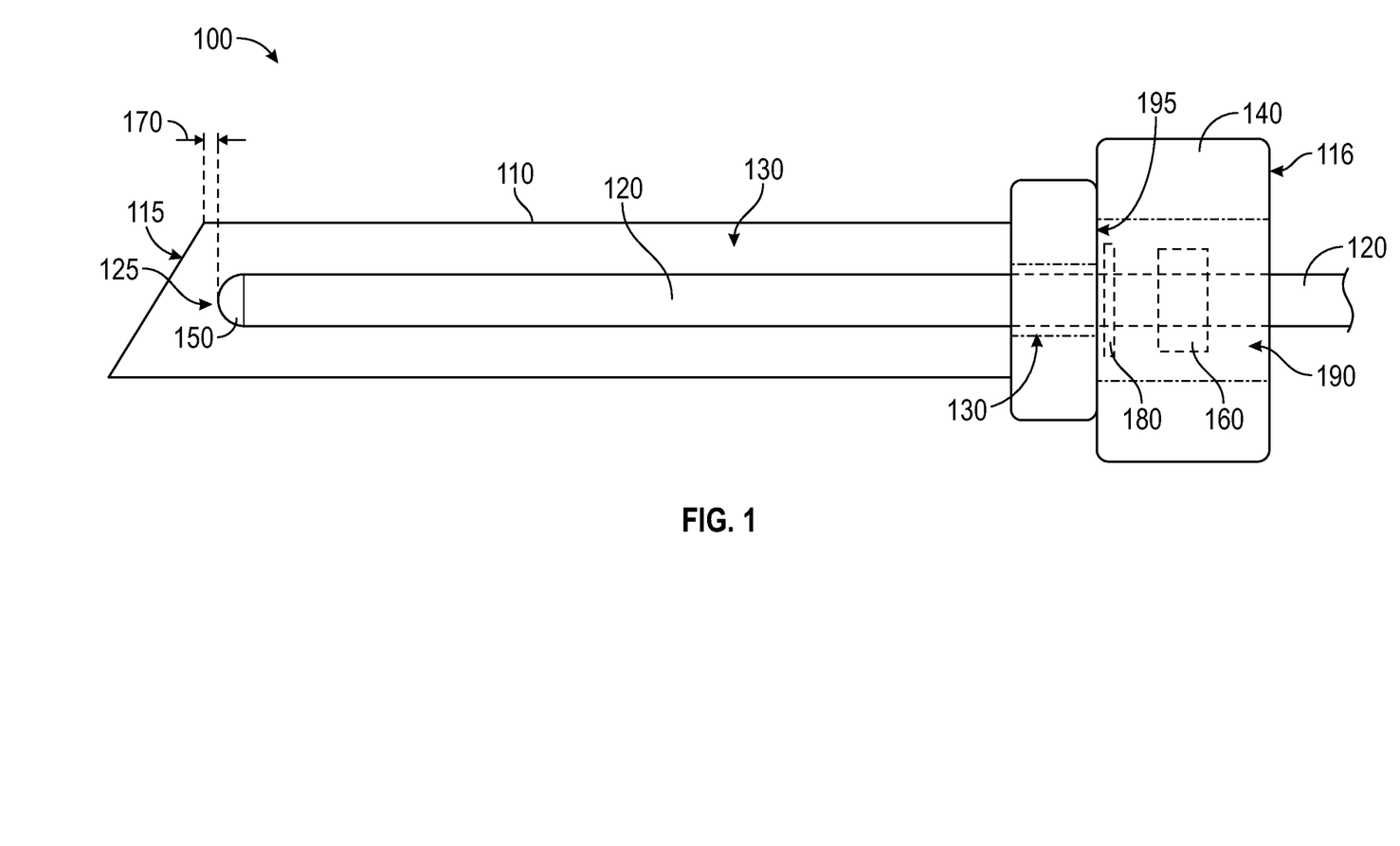
FIG. 1 shows a schematic view of a puncture visualization device.

FIG. 1 shows a schematic view of portions of a puncture visualization device 100. The puncture visualization device 100 can include a needle 110 and a guidewire 120. The needle 110 can facilitate gaining access to internal anatomy of a patient. For example, the needle 110 can puncture tissue anatomy (e.g., skin, muscle, fat, organs, or the like) of a patient during a medical procedure, for instance a percutaneous nephrolithotomy procedure. The needle 110 can receive the guidewire 120, and the needle 110 can facilitate locating a distal portion of the guidewire 120 in the anatomy of the patient. For example, a needle lumen 130 can receive the guidewire 120, and the needle can puncture a path toward the target with the guidewire 120 received in the needle lumen 130.

For example, the needle 110 can receive the guidewire 120 for use during a puncture procedure. The needle can be guided to the target (e.g., a calyx of a kidney, or the like). A target area can optionally be externally imaged (e.g., with fluoroscopy, x-rays, or the like) such as to help guide the needle 110 (and the guidewire 120) toward the target. The needle 110 can be removed (e.g., by withdrawing the needle 110) such as while maintaining the location of the distal portion of the guidewire 120 in the anatomy of the patient. Accordingly, the needle 110 can help facilitate locating a distal portion of the guidewire 110 in the anatomy of the patient.

With the distal portion of the needle 110 located in the anatomy of a patient, the guidewire 120 can facilitate locating (e.g., placement, positioning, inserting, withdrawing, moving, translating, or the like) one or more other medical instruments in the anatomy of the patient. For instance, a catheter, nephoroscope, or the like can be coupled with the guidewire 120, and translated with respect to (e.g., slid along, or the like) the guidewire 120. Accordingly, the guidewire 120 can facilitate one or more medical procedures (e.g., kidney stone removal, or the like), such as with the one or more other medical instruments.

FIG. 1 shows the needle 110 as including a needle hub 140. The needle lumen 130 extends through the needle hub 140 (with such portion shown in broken lines in FIG. 1). The needle hub 140 can receive the guidewire 120. The needle hub 140 can help facilitate coupling the needle 110 with one or more other medical devices (e.g., tubing, a syringe, a catheter, or the like). The needle hub 140 can inhibit relative motion between the guidewire 120 and the needle 110, for example with a lock that inhibits relative motion between the guidewire 120 and the needle 110.

The puncture visualization device 100 can help facilitate puncturing along a path toward the target with the needle 110, for instance by providing a distal field of view from an on-board location within the needle lumen 130 of the needle 110 (or from an exterior of the needle 110, such as from the needle hub 140, or the like). The distal field of view can be located at or near or beyond a distal end 115 of the needle 110. The distal field of view can provide a user with visualization that can help facilitate puncturing toward the target with the distal end 115 of the needle 110.

The needle lumen 130 can receive a portion of the guidewire 120. The distal portion or distal end of the guidewire 120 can include an optical sensor 150 (e.g., such as can include one or more of a camera, image sensor, optical source, or the like) such as can be used to provide visualization information, for example at a distal tip 125 of the guidewire 120, such as can be communicated as a visualization signal along the guidewire such as to an external display viewable by a user. For example, with the distal portion of the guidewire 120 received in the needle lumen 130, the optical sensor 150 can provide the distal field of view, such as when the optical sensor 150 is located near the distal end 115 of the needle 110. Accordingly, the needle 110 and the guidewire 120 (including the optical sensor 150) can be positioned with respect to each other to cooperate to provide the distal field of view, which, in turn can help facilitate puncturing toward a target with the needle 110.

FIG. 1 shows the needle hub 140, which can inhibit relative motion between the guidewire 120 and the needle 110. The needle hub 140 can include a lock 160, and the lock 160 can position or help inhibit (e.g., secure, fix, fasten, hold, maintain, or the like) the relative motion between the guidewire 120 and the needle 110. For example, the lock 160 can secure the location of the guidewire 120 relative to the needle 110 (e.g., to fix the location of a portion of the guidewire 120 within the needle lumen 140). The optical sensor 150 can be coupled to the needle 110. For example, the optical sensor 150 can be included in the needle hub 140. The optical sensor 150 can be coupled to an exterior of the needle 110.

The needle lumen 130 can receive a portion of the guidewire 120, and the distal tip 125 of the guidewire 120 can be located near the distal end 115 of the needle 110. Accordingly, the puncture visualization device 100 can provide a distal field of view, for example using the optical sensor 150 located within the needle lumen 130 and near the distal end 115 of the needle 110. Unless secured, the guidewire 120 can move relative to the needle 110, for example during a puncture procedure with the needle 110. Relative motion between the guidewire 120 and the needle 110 can alter the field of view provided by the optical sensor 150. For example, the location of the optical sensor 150 relative to the distal end 115 of the needle 110 could change due to the relative motion between the guidewire 120 and the needle 110. Such change in location of the optical sensor 150 relative to the distal end 115 can change the field of view provided by the puncture visualization device 100 (e.g., by changing the field of view away from a specified field of view).

The lock 160 can inhibit relative motion between the guidewire 120 and the needle 110, for instance to maintain the location of the optical sensor 150 within the needle lumen 130 at a specified offset 170 from the distal end 115 of the needle 110. As a result, the lock 160 facilitates puncturing the target with the needle 110 while the optical sensor 150 provides the distal field of view from a location within the needle 110 (e.g., with the optical sensor 150 located within the needle lumen 130). In some examples, the lock 160 facilitates providing a specified (e.g., constant, set, fixed, static) field of view, for instance by maintaining the location of the optical sensor 150 within the needle lumen 130 at the specified offset 170 from the distal end 115 of the needle 110. The specified offset 170 can be user-adjustable, for example by operating the lock to adjust a position of the guidewire 120 with respect to the needle 110. Maintaining the specified distal field of view from a location within the needle lumen 130 of needle 110 can enhance guidance of the needle 110 toward the target, for instance because the field of view does not change due to relative motion between the guidewire 120 and the needle 110. For example, the lock 160 can enhance depth perception for the user of the puncture visualization device 100 by maintaining the specified offset 170 of the image sensor 150 from the distal end 115 of the needle 110. Accordingly, the puncture visualization device 100 can help enhance guidance of the needle 110 toward a target, which facilitates puncturing the target or along a path toward the target with the needle 110.

FIG. 1 shows a puncture visualization device 100 that can include an alignment feature 180 (e.g., a ridge, key, keyway, stop, protrusion, boss, or the like). The alignment feature 180 can help facilitate positioning the optical sensor 150 at the specified offset 170 from the distal end 115 of the needle 110. More particularly, a change in location of the optical sensor 150 relative to the distal end 115 can change the field of view provided by the puncture visualization device 100. The alignment feature 180 can help provide the specified offset 170 between the optical sensor 150 and the distal end of the needle 115, for instance to provide a specified (e.g., consistent, repeatable, steady, or the like) field of view from within the needle 110 and enhance visualization with the puncture visualization device 100.

For example, the guidewire 120 can include the alignment feature 180, and the alignment feature 180 can extend (e.g., radially, or the like) from the guidewire 120. The alignment feature 180 can engage with one or more other components of the puncture visualization device 100 such as to position the optical sensor 150 at the specified offset 170 from the distal end 115 of the needle 110. For example, the alignment feature 180 can engage with the needle hub 140 with guidewire 120 received in the needle lumen 130. In an example, the alignment feature can inhibit over insertion, under insertion, or the like of the guidewire 120 within the needle lumen 130 of the needle 110. The alignment feature 180 can facilitate consistently establishing a desired field of view for the optical sensor 150.

The puncture visualization device 100 can include a complementary connector 190. The complementary connector 190 can cooperate with the alignment feature 180 such as to position the optical sensor 150 at the specified offset 170 from the distal end 115 of the needle 110. For instance, the needle hub 140 can include the complementary connector 190, and the complementary connector 190 can engage the alignment feature 180. The alignment feature 180 can engage the complementary connector 190 (e.g., the alignment feature 180 can receive, or be received by, the complementary connector 190). Accordingly, the alignment feature 180 can engage with the complementary connector 190 to facilitate positioning the optical sensor 150 at the specified offset 170. An example of complementary connectors can include male and female complementary connectors, which can be interchanged, if desired. Other examples of complementary connectors can include one or more threads, or the like, which can similarly be interchanged, if desired.

For instance, a proximal end 116 of the needle 110 may include the needle hub 140 and the complementary connector 190. The alignment feature 180 can engage with an alignment face 195 of the complementary connector 190 such as to position the optical sensor 150 at the specified offset 170 from the distal end 115 of the needle 110. The needle lumen 130 may receive the guidewire 120 while inhibiting reception of the alignment feature 180 by the needle lumen (e.g., because the alignment feature engages with the alignment face 195 of the complementary connector 190). The lock 180 can engage with guidewire 120 to maintain the specified offset 170 with the alignment feature 180 engaged with the alignment face 195 of the complementary connector 190. Accordingly, the puncture visualization device 100 can facilitate positioning the optical sensor 150 at the specified offset 170 from the distal end 115 of the needle 110 (and maintaining the optical sensor 150 at the specified offset 170).

Figure 2A:
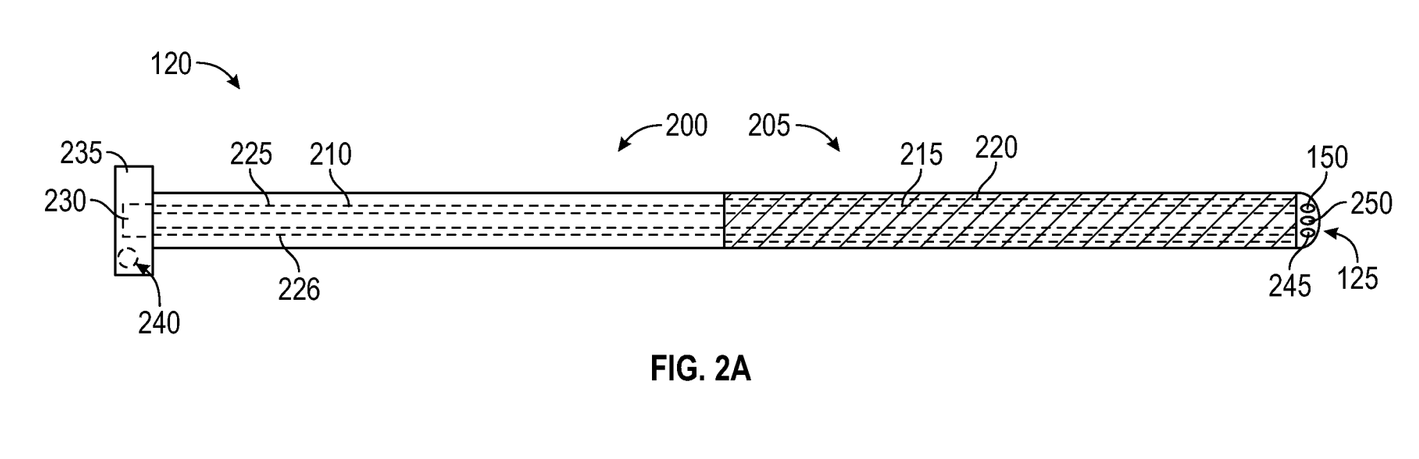
FIG. 2A shows a schematic view of a guidewire.

FIG. 2A shows a schematic view of portions of the guidewire 120. The guidewire 120 has a proximal section 200 and a distal section 205 including the distal tip 125. The proximal section 200 can include a polymer sleeve 210 (e.g., such as to protect the guidewire 120 or reduce a frictional coefficient of an exterior surface of the guidewire 120). The distal section 205 of the guidewire 120 can include a distal coil 215. The distal coil 215 can cooperate with an inner support 220 (such as shown in broken lines in FIG. 2A) such as to enhance the mechanical strength to the guidewire 120 (e.g., to enhance pushability of the guidewire 120, or to reduce or minimize kinking of the guidewire 120). For instance, the inner support 220 can engage with the distal coil 215 such as to enhance the mechanical strength of the guidewire 120.

The distal coil 215 can include a plurality of filars. For instance, the multi-filar distal coil 215 can enhance smoothness of an external surface of the guidewire 120. The plurality of filars can facilitate a smooth tactile feel, for instance to reduce non-uniformity of movement of the guidewire 120. For example, the plurality of filars can reduce jerky movement, stuttering, or the like when the guidewire 120 is moved relative to the needle 110 with the guidewire 120 received in the needle lumen 130 of the needle 110, shown in FIG. 1). For instance, the plurality of filars can facilitate smoothly translating the guidewire 120 within the needle lumen 130.

The distal coil 215 can include a flat wire or a tube. The distal coil 215 can include a polymer. Materials for the distal coil 215 can be varied and can be used in combination, for example to create a hybrid assembly for enhanced or tailored radiopacity and physical performance. The distal coil 215 can include a single layer or can include multilayer construction. The distal coil 215 can be covered with a flexible polymer tube, for example to enhance torque control, axial stability, or physical performance of the guidewire 120. In another example, the guidewire 120 can include a metallic tube, for instance to provide flexibility, torque control, or axial stability.

The inner support 220 can define an aperture (e.g., a hollow area, a lumen, or the like). In an example, the inner support 220 includes a coil, and the coil of the inner support 220 can be wound in an opposite direction of the distal coil 215 (e.g., such as to enhance the mechanical strength of the guidewire 120). For instance, the distal coil 215 can be wound in a clockwise direction, and the inner support 220 can be wound in a counter-clockwise direction.

The guidewire 120 can include the optical sensor 150. The guidewire 120 can include a first optical fiber 225 (or a plurality of optical fibers). The inner support 220 can surround the optical fiber 225 (e.g., the inner support 220 can receive the optical fiber 225). The optical fiber 225 can facilitate transmission of an optical signal representing the distal field of view provided by the optical sensor 150. For instance, the optical fiber 225 can transmit one or more illumination or visualization optical signals between the optical sensor 150 and a transducer 230. The transducer 230 can convert one or more visualization optical signals corresponding to the distal field of view provided by the optical sensor 150 (and the optical fiber 225) to one or more electrical signals corresponding to the distal field of view.

The optical sensor 150 be a transducer (e.g., the optical sensor can include circuitry similar to transducer 230). For instance, the optical signal can be converted into an electrical signal right at the optical sensor 150 (e.g., with incident light generating an electrical response, such as with a charge coupled device in which incident photons generate electrons). In such case, there can need to be one or more electrical wires extending along the guidewire to communicate the electrical signals representing the image to the proximal end of the guidewire 120 and to an external display. The wires can be located in the guidewire 120 (e.g., in an aperture defined by the inner support 220). The optical fiber 225 can be located in the guidewire 120.

The guidewire 120 can include a second optical fiber 226. The optical fiber 226 (which can be included in a plurality of guidewires) can provide visualization information, for example visualization information at the distal tip 125 of the guidewire 120. In an example, the guidewire 120 may not include the optical sensor 150. For instance, the guidewire 120 may not have space to accommodate the optical sensor 150. The optical fiber 226 can be located at the distal tip 125 (e.g., by terminating the optical fiber 226 at the distal tip 125, or the like). The optical fiber 226 can transmit visualization information through the guidewire 120, for example by transmitting the visualization information to a display. Accordingly, the optical fiber 226 can provide visualization information, for instance when the guidewire 120 does not include the optical sensor 150. In an example, dimensions of the distal tip 125 can be reduced where the optical fiber 226 provides visualization information (in comparison to the optical sensor 150 providing visualization information).

The guidewire 120 can include a guidewire connector 235, and the guidewire connector 235 can facilitate interconnecting the guidewire 120 (and the optical sensor 150) with one or more other components of the puncture visualization device 100. For example, the guidewire connector 235 can include one or more electrical interconnects 240 that transmit the electrical signals provided by transducer 230 to other components of the puncture visualization device 100. A cable can interconnect with the guidewire connector 235 to transmit the electrical signals corresponding to the distal field of view (provided by the optical sensor 150) to a display (e.g., an LCD screen, or the like). The display can facilitate visualization during puncturing of the target, for example by presenting the distal field of view provided by the optical sensor 150 on the display.

FIG. 2A shows the guidewire 120, which can include a light source 245, for example located at the distal tip 125 of the guidewire 120. For example, the optical fiber 225 can communicate illumination lighting to provide the light source 245. In an example, the optical fiber 225 can be coupled to the light source 245 and the optical fiber 225 can transmit light to the light source 245.

In some examples, the guidewire 120 may not include the light source 245. For example, the light source 245 can be external to (e.g., distal to, remote from, a separate component, or the like) the guidewire 120. The optical fiber 225 can be coupled to the light source 245. The optical fiber 225 can facilitate transmission of light from the light source 245 to the distal tip 125 of the guidewire 120 (e.g., to illuminate an area proximate the distal tip 125).

The guidewire can include one or more additional sensors 250, for example the optical sensor 150. The additional sensors 250 can be located at the distal tip 125 of the guidewire. Such sensors 250 can include a force sensor, such as to detect a force applied to the distal tip 125. The sensors 250 can include a temperature sensor, for instance to determine a temperature at or near the distal tip 125 of the guidewire 120.

Figure 2B:
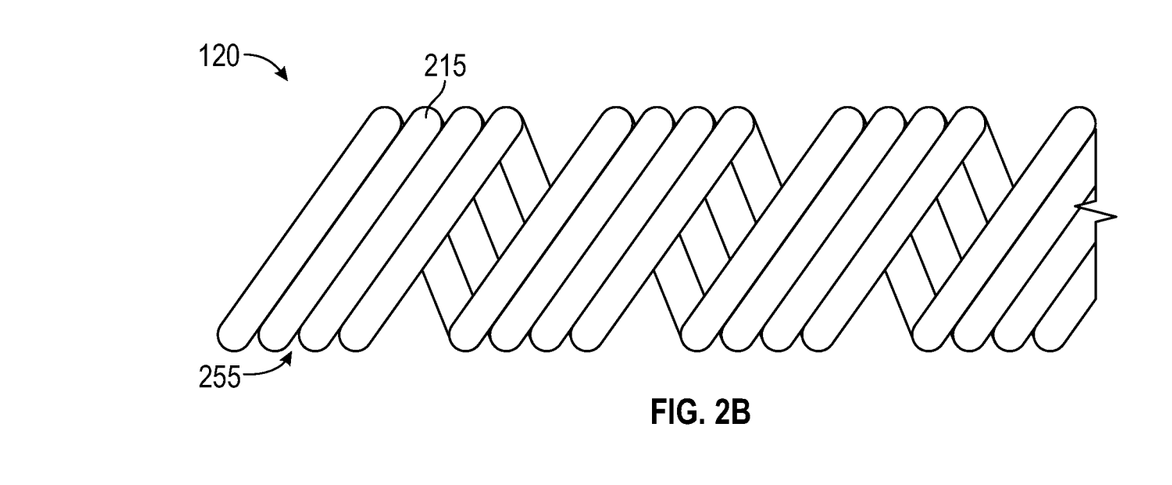
FIG. 2B shows a side view of an example of the distal coil 215.

FIG. 2B shows a side view of an example of the distal coil 215. FIG. 2B shows the distal coil 215 including a plurality of filars 255. The plurality of filars 255 can facilitate a smooth tactile feel, for instance to reduce non-uniformity of movement of the guidewire 120 (e.g., when the guidewire 120 is moved relative to the needle 110 with the guidewire 120 received in the needle lumen 130 of the needle 110, shown in FIG. 1). The distal coil 215 can be wound in a first direction (e.g., clockwise), and the inner support 220 (shown in FIG. 2A) can be wound in a second direction (e.g., counter-clockwise).

Figure 3A:
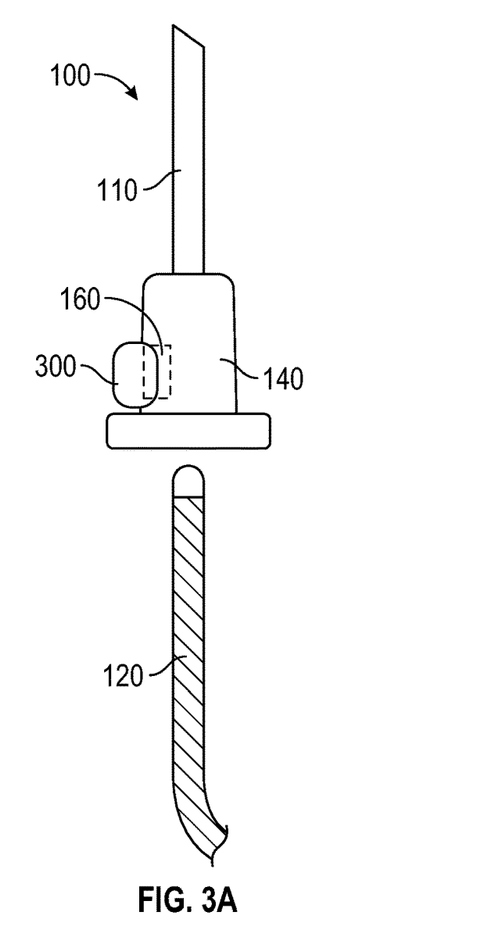
FIG. 3A shows a side view of an example of the puncture visualization of FIG. 1 including a lock.

FIG. 3A shows a side view of an example of the puncture visualization 100 of FIG. 1 including the lock 160. As described herein, the lock 160 inhibits relative motion between the guidewire 120 and the needle 110. For example, the needle hub 140 can include an actuator 300, and the actuator 300 can facilitate operation of the lock 160. A user can engage with the actuator 300 to transition the puncture visualization device 100 between a locked configuration and an unlocked configuration. In the locked configuration, the lock 160 can engage with the guidewire 120 to inhibit relative motion between the guidewire 120 and the needle 110 (e.g., to maintain the optical sensor 150 at the specified offset 170 from the distal end of the needle 110, shown in FIG. 1). In the unlocked configuration, the lock 160 is disengaged from the guidewire 120, for example to allow relative motion between the guidewire 120 and the needle 110 (e.g., to facilitate withdrawal and decoupling of the needle from guidewire 120). FIG. 3A shows the puncture visualization device 100 in the unlocked configuration, with the actuator 300 extending from the needle hub 140 (e.g., the actuator 300 is popped out).

As described herein, a user can engage with (e.g., push, depress, twist, pull, or the like) the actuator 300 to transition the device 100 between the unlocked configuration and the locked configuration. With a portion of the guidewire 120 received in the needle lumen 130 (shown in FIG. 1), user engagement with the actuator 300 can transition the device 100 from the unlocked configuration to the locked configuration and engage the lock 160 with the guidewire 120. In an example, user engagement with the actuator can transition the device 100 from the locked configuration to the unlocked configuration and disengage the lock 160 from the guidewire 120.

Figure 3B:
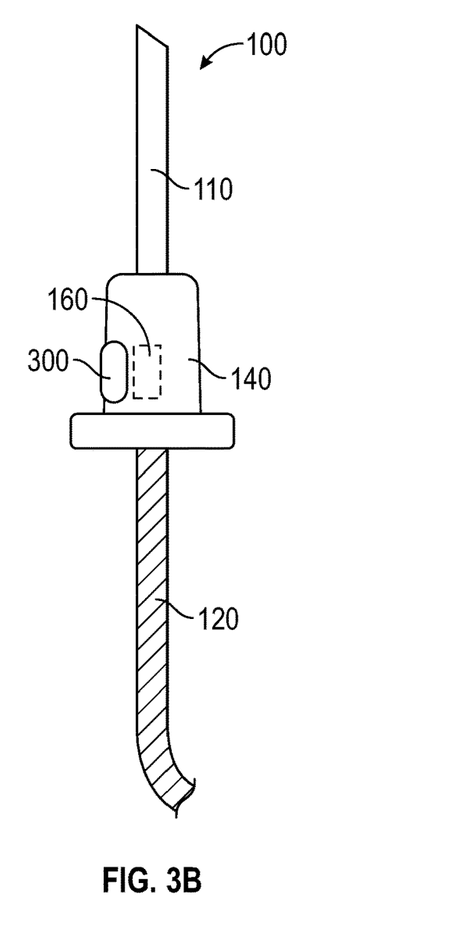
FIG. 3B shows another side view of the puncture visualization device of FIG. 3A.

FIG. 3B shows a side view of the puncture visualization device 100 of FIG. 3A. FIG. 3A shows the puncture visualization device 100 in the locked configuration, with the guidewire 120 received by the needle 110, and with the actuator 300 depressed (e.g., pushed in from the position shown in FIG. 3A). Accordingly, the actuator 300 facilitates transitioning the puncture visualization deice 100 between the locked configuration and the unlocked configuration, for example to inhibit relative motion between the guidewire 120 and the needle 110.

Figure 3C:
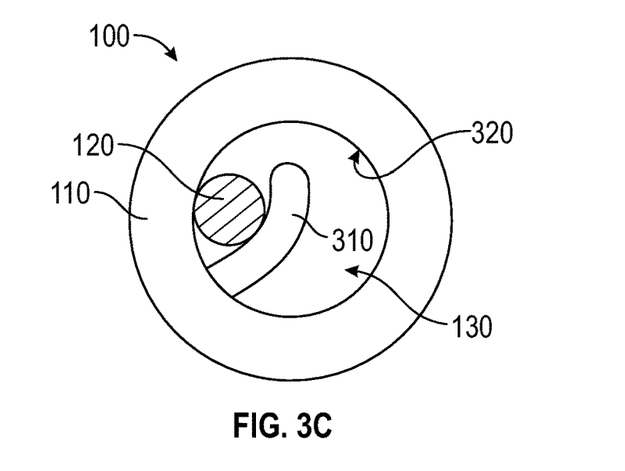
FIG. 3C shows a schematic view of the puncture visualization device of FIG. 3A.

FIG. 3C shows a schematic view of the puncture visualization device 100 of FIG. 3A. The lock 160 can extend into the needle lumen 130 of the needle 110. For example, the lock 160 can include an arm 310, and the arm 310 can extend into the needle lumen 130. The arm 310 can engage with the guidewire 120 to inhibit relative motion between the guidewire 120 and the needle 110. In an example, engagement with the actuator 300 (shown in FIGS. 3A and 3B) can compress the guidewire 120, for example by compressing the guidewire 120 between the arm 310 and a wall 320 of the needle lumen 130. Accordingly, the lock 160 can inhibit relative motion between the guidewire 120 and the needle 110.

The arm 310 can be biased, for example to engage with the guidewire 120 and inhibit relative motion of the guidewire 120. In some examples, the needle hub 140 does not include the actuator 300, and a user can engage the guidewire 120 with the arm 310 to inhibit motion of the guidewire. The user can disengage the guidewire 120 from the arm 310 to facilitate movement of the guidewire 120.

Figure 4A:
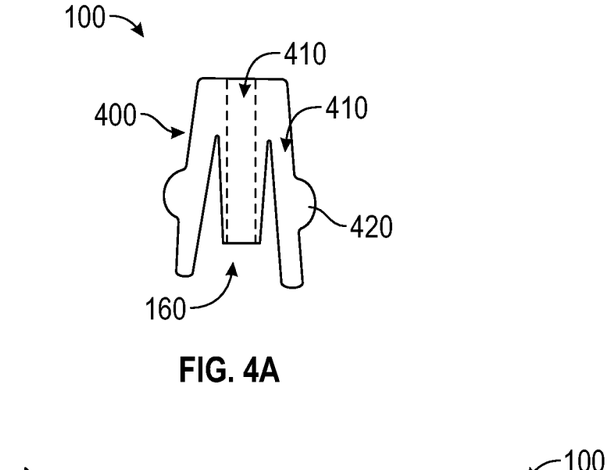
FIG. 4A shows a side view of an example of a guidewire adaptor for the puncture visualization device.

FIG. 4A shows a side view of an example of a guidewire adaptor 400 for the puncture visualization device 100. The guidewire adaptor 400 can receive the guidewire 120 (shown in FIG. 4B). For instance, the guidewire adaptor 400 can include an adaptor lumen 410 that receives the guidewire 120. The guidewire adaptor 400 can engage with the needle hub 140 (shown in FIG. 4C), for example to selectively couple the guidewire adaptor 400 with the needle hub 140. The guidewire adaptor 400 can include one or more arms 420 (e.g., wings, tabs, legs, levers, or the like) that can engage with the needle hub 140 to couple the guidewire adaptor with the needle hub 140. In an example, the arms 420 can be operated (e.g., squeezed, compressed, opened, or the like) to disengage the arms 420 from the needle hub 120 and accordingly facilitate decoupling the guidewire adaptor 400 from the needle hub 140.

The guidewire adaptor 400 can include the lock 160. For instance, the lock 160 can engage with the guidewire 120 (shown in FIG. 4B) to inhibit relative motion between the guidewire 120 and the needle 110. In an example, the needle lumen 410 can receive the guidewire 120. The lock 160 can engage with the guidewire 120, for instance when the guidewire adaptor 400 is selectively coupled with the needle hub 140. Accordingly, selectively coupling the guidewire adaptor 400 with the needle hub 140 can facilitate transitioning the puncture visualization device 100 between the unlocked configuration and the locked configuration.

Figure 4B:
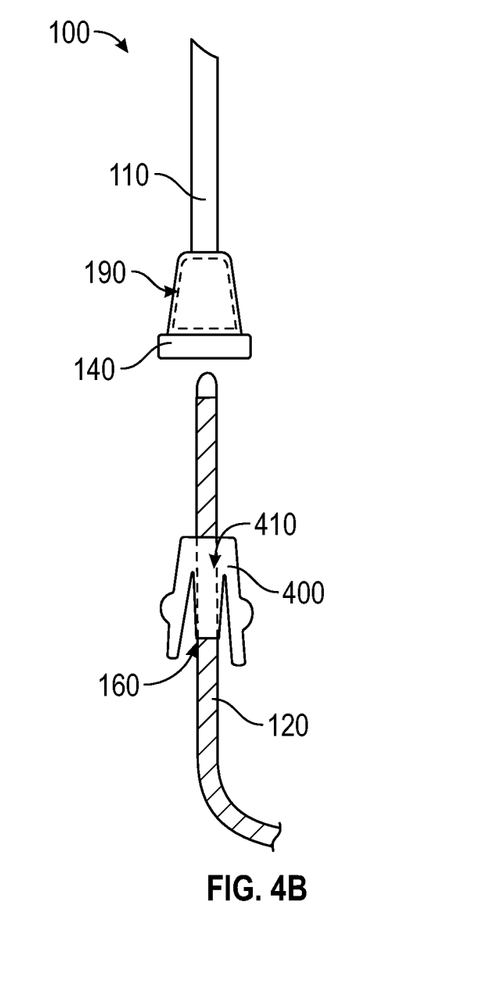
FIG. 4B shows a side view of the puncture visualization device including the guidewire adaptor of FIG. 4A.

FIG. 4B shows a side view of the puncture visualization device 100 including the guidewire adaptor 400 of FIG. 4A. As described herein, the adaptor lumen 410 can receive the guidewire 120. The guidewire adaptor 400 can include the lock 160, and the lock 160 can engage with the guidewire 120 to inhibit relative motion between the guidewire 120 and the needle 110. In an example, the guidewire adaptor 400 can compress the guidewire 120 within the adaptor lumen 400, for instance when the guidewire adaptor 400 is selectively coupled with the needle hub 140. In another example, selectively coupling the guidewire adaptor 400 with the needle hub 140 can change a cross section of the needle hub 140 (and correspondingly compress the guidewire 120 within the adaptor lumen 410). In yet another example, the guidewire 120 can be compressed between the arms 420 with the guidewire adaptor 400 selectively coupled with the needle hub 140.

The needle hub 140 can include the complementary connector 190, and the complementary connector 190 may receive the guidewire adaptor 120. For example, the complementary connector 190 can receive the guidewire adaptor 400 with the guidewire 120 received in the adaptor lumen 410. The guidewire adaptor 400 can engage with the complementary connector 190, for instance to selectively couple the guidewire adaptor 400 with the needle hub 140 (shown in FIG. 4C). The selective coupling of the guidewire adaptor 400 with needle hub 140 can inhibit the relative motion between the guidewire 120 and the needle 110, for example to maintain the specified offset 170 of the optical sensor 150 from the distal end 115 of the needle 110 (shown in FIG. 1).

Figure 4C:
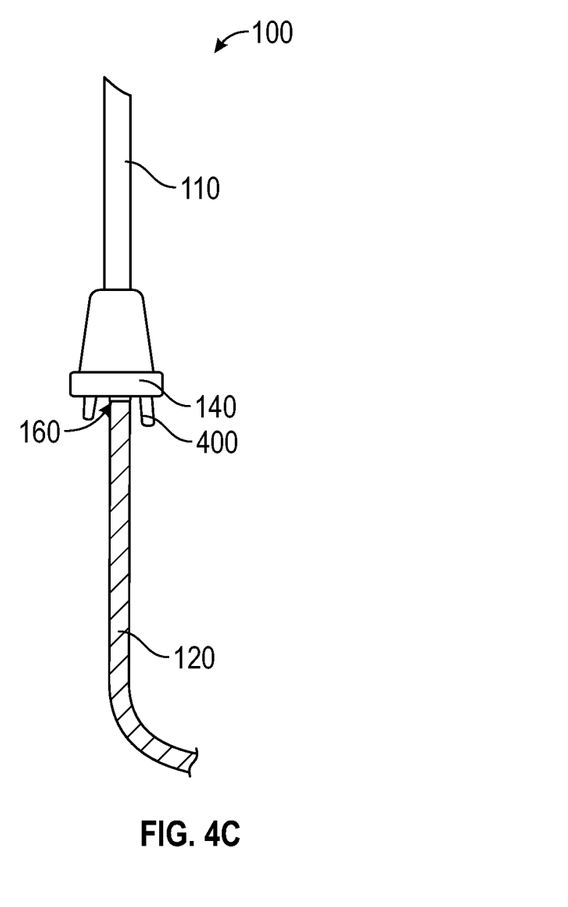
FIG. 4C shows another side view of the puncture visualization device including the guidewire adaptor of FIG. 4A.

FIG. 4C shows another side view of the puncture visualization device 100 including the guidewire adaptor 400 of FIG. 4A. FIG. 4C shows the guidewire received by the guidewire adaptor 400 and the needle 110. The lock 160 can engage with the guidewire 120 with the guidewire adaptor 400 selectively engaged with the needle hub 140. Accordingly, the guidewire adaptor 400 and the needle hub 140 can cooperate to inhibit relative motion between the guidewire 120 and the needle 110 with the guidewire 120 received by the guidewire adaptor 400 and by the needle 110.

Figure 5:
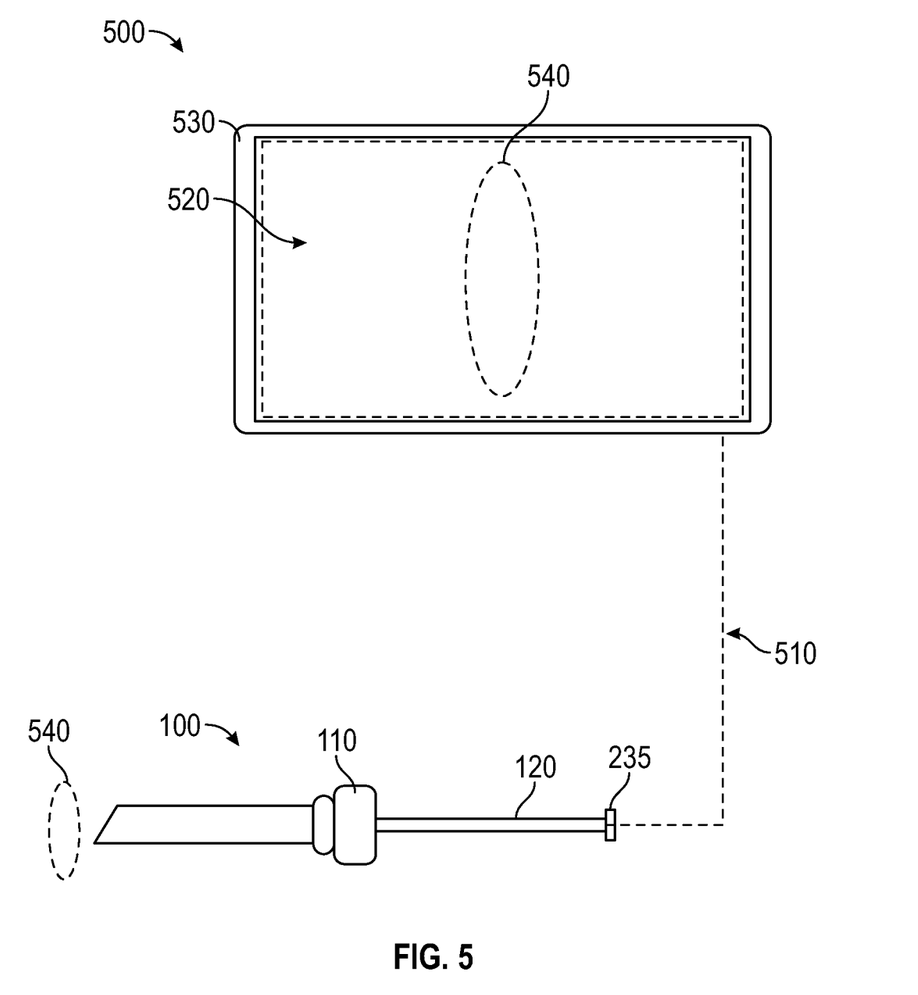
FIG. 5 shows a schematic view of an example of a puncture visualization system.

FIG. 5 shows a schematic view of an example of a puncture visualization system 500. As described herein, the guidewire 120 can include a guidewire connector 235, and the guidewire connector 235 can facilitate interconnecting the guidewire 120 (and the optical sensor 150, shown in FIG. 1) with other components of the puncture visualization device 100 or the puncture visualization system 500. For example, a cable 510 (shown in dashed lines in FIG. 5) can interconnect with the guidewire connector 235 to transmit the electrical signals corresponding to a distal field of view 520 (shown in dashed lines in FIG. 5) to an image signal processing device such as can be used to generate a resulting image that can be displayed on a display 530 (e.g., any suitable display, such as can include one or more of an LCD screen, LED screen, television, monitor, tablet, smartphone, or the like). The display 530 can facilitate visualization during puncturing of the target, for example by presenting the distal field of view 520 (including an image of an anatomical feature 540, for instance a fat layer, an organ, or the like) provided by the optical sensor 150 (shown in FIG. 1) on the display 530.

Figure 6:
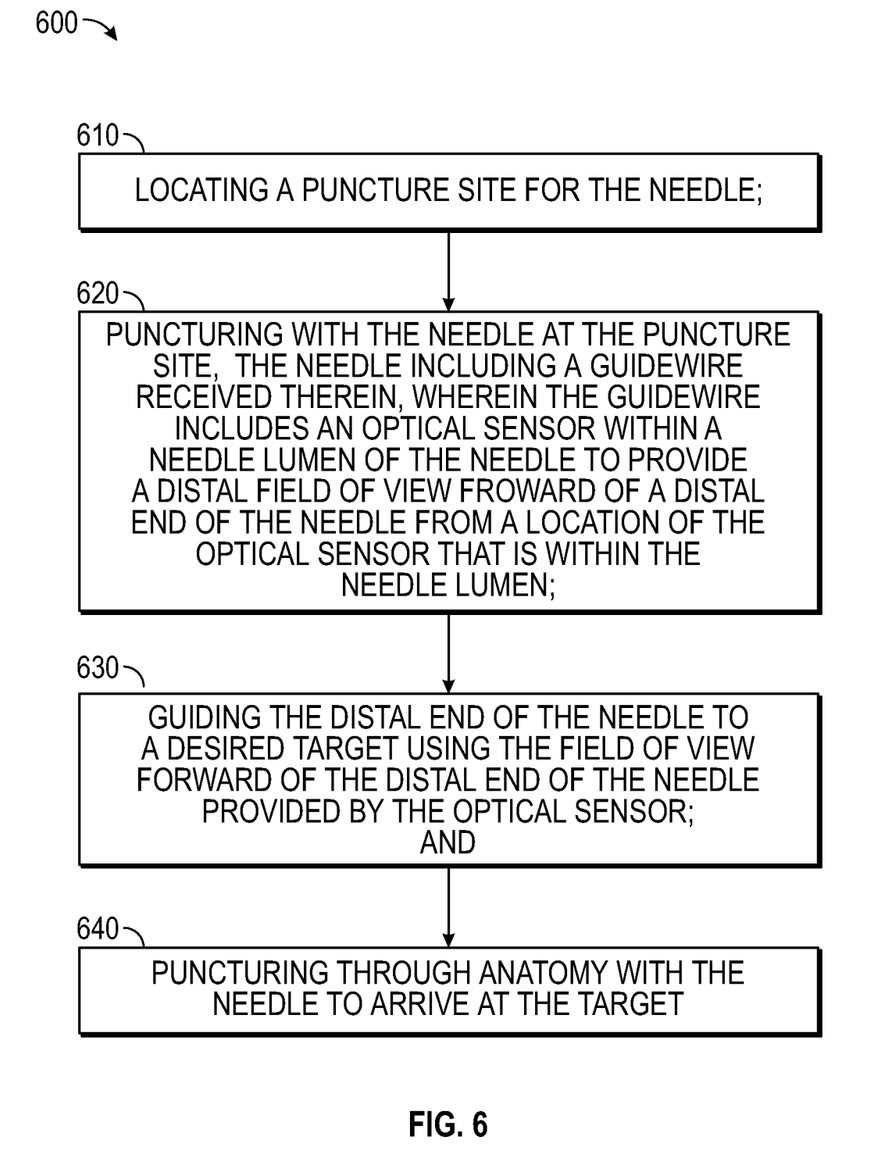
FIG. 6 shows an example of a method for visualizing during puncture by a needle.

FIG. 6 shows an example of a method 600 for visualizing during puncture by a needle 110, including one or more of the puncture visualization device 100 or the puncture visualization system 500 described herein. In describing the method 600, reference is made to one or more components, features, functions and operations previously described herein. Where convenient, reference is made to the components, features, operations and the like with reference numerals. The reference numerals provided are exemplary and are not exclusive. For instance, components, features, functions, operations, procedures and the like described in the method 600 include, but are not limited to, the corresponding numbered elements provided herein and other corresponding elements described herein (both numbered and unnumbered) as well as their equivalents.

The method 600 can include at 610 locating a surface puncture site (e.g., a portion of skin on a back of a patient, or the like) for the needle 110. In an example, locating the surface puncture site for the needle can include imaging of a target area including the target including other than using the optical sensor 150. For example, the target area can be imaged with fluoroscopy, x-rays, magnetic resonance imaging, or the like. A path between the surface puncture site and the target can be identified, for example with the imaging of the target area.

At 620, the needle 110 can puncture the surface puncture site. The needle 110 can include a guidewire 120 received therein, for example within a needle lumen 130 of the needle 110. The guidewire 120 can include an optical sensor 150 within the needle lumen 130. The optical sensor 150 can provide a distal field of view 520, for instance forward of a distal end 115 of the needle 110. The optical sensor 150 can provide the distal field of view 520 from a location within the needle lumen 130. The method 600 can include at 630 guiding the distal end 115 of the needle 110 to a target using the distal field of view 520 provided by the optical sensor 150. For example, the distal field of view 520 can facilitate guiding the needle 110 along the path between the surface puncture site and the target. At 640, the needle 110 can puncture through anatomy to arrive at the target.

Several options for the method 600 follow. For example, the optical sensor 150 can be positioned within the needle lumen 130 at a specified offset 170 from the distal end 115 of the needle 110. In an example, an alignment feature 180 of the guidewire 120 can engage with the needle 110 to facilitate alignment of the optical sensor 150 within the needle lumen at the specified offset 170 from the distal end 115. In yet an example, a lock 160 is engaged with the guidewire 120 to inhibit relative motion between the guidewire 120 and the needle 110. For instance, engaging the lock with the guidewire can include engaging an actuator 300 to transition the puncture visualization device 100, including the needle 110, between a locked configuration and an unlocked configuration. Further, the method 600 can include engaging the guidewire 120 with a guidewire adaptor 400, for example by receiving the guidewire 120 within an adaptor lumen 410 of the guidewire adaptor 400. In another example, the method 600 includes compressing the guidewire in the adaptor lumen, for instance to inhibit relative motion between the guidewire and the needle 110 when the guidewire adaptor 400 is selectively coupled with a needle hub 140.

Still further, the method 600 can include inserting the guidewire 120 into the needle lumen 130 of the needle 110. In another example, the method 600 includes coupling the guidewire 120 with a catheter. In yet another example, the needle provides a puncture hole, and the puncture hole can be dilated (e.g., incrementally increasing a diameter of the puncture hole, for example with a balloon dilator, dilator sheathe, or the like).

Various Notes & Aspects

Aspect 1 is a puncture visualization device for a percutaneous puncturing procedure, the puncture visualization device comprising: a guidewire, including: a proximal section; a distal section including a distal coil and a distal tip; an inner support engaged with the distal coil; a needle including a needle lumen configured to receive the guidewire; a lock configured to engage with the guidewire to inhibit relative motion between the guidewire and the needle; and an optical sensor, located at the distal tip of the guidewire, the optical sensor configured to be locked into a position by the lock to provide a distal field of view from a location within the needle and near a distal end of the needle for visualization to facilitate puncturing a target with the distal end of the needle.

In Aspect 2, the subject matter of Aspect 1 optionally includes wherein the guidewire includes a first alignment feature to facilitate positioning of the optical sensor within the needle lumen at a specified offset from a distal end of the needle.

In Aspect 3, the subject matter of any one or more of Aspects 1-2 optionally include a needle hub at a proximal end of the needle and included within a needle lumen of the needle.

In Aspect 4, the subject matter of Aspect 3 optionally includes wherein the needle hub includes: the lock; and an actuator configured to transition the puncture visualization device between a locked configuration and an unlocked configuration, wherein: in the locked configuration, the lock is engaged with the guidewire; and in the unlocked configuration, the lock is disengaged from the guidewire.

In Aspect 5, the subject matter of Aspect 4 optionally includes wherein the lock includes an arm configured to engage with the guidewire and bias the guidewire toward a wall of the needle lumen.

In Aspect 6, the subject matter of any one or more of Aspects 3-5 optionally include a guidewire adaptor including the lock, wherein: the guidewire adaptor includes an adaptor lumen configured to receive the guidewire; and the needle hub is configured to receive the guidewire adaptor, wherein: the guidewire adaptor is configured to engage with the needle hub to selectively couple the guidewire adaptor with the needle hub; and the lock is configured to engage with the guidewire when the guidewire adaptor is coupled with the needle hub.

In Aspect 7, the subject matter of Aspect 6 optionally includes wherein the lock is configured to compress the guidewire in the adaptor lumen to inhibit the relative motion between the guidewire and needle when the guidewire adaptor is selectively coupled with needle hub.

In Aspect 8, the subject matter of any one or more of Aspects 1-7 optionally include wherein the inner support includes an inner coil.

In Aspect 9, the subject matter of Aspect 8 optionally includes wherein the inner coil is wound in a first direction, and the distal coil is wound in a second direction opposite the first direction.

In Aspect 10, the subject matter of any one or more of Aspects 8-9 optionally include wherein the inner coil defines an interior chamber and the optical sensor is located at least partially within the interior chamber defined by the inner coil.

In Aspect 11, the subject matter of any one or more of Aspects 1-10 optionally include wherein the distal coil has a rounded profile.

In Aspect 12, the subject matter of any one or more of Aspects 1-11 optionally include wherein the guidewire includes a light source configured to illuminate an area distal to the distal tip of the guidewire.

In Aspect 13, the subject matter of Aspect 12 optionally includes wherein the guidewire includes an optical fiber providing or coupled to the light source.

In Aspect 14, the subject matter of any one or more of Aspects 1-13 optionally include an electrical interconnect in communication with the optical sensor and included in the proximal section of the guidewire.

In Aspect 15, the subject matter of any one or more of Aspects 1-14 optionally include one or more of a temperature sensor or a force sensor located at the distal tip of the guidewire.

In Aspect 16, the subject matter of any one or more of Aspects 1-15 optionally include a seal configured to engage with the guidewire and inhibit flow between the needle lumen and the guidewire.

Aspect 17 is a puncture visualization device for a percutaneous puncturing procedure, the puncture visualization device comprising: a guidewire, including: a proximal section; a distal section including a distal coil and a distal tip; an inner support engaged with the distal coil; and wherein: the guidewire is configured to be inserted in a lumen of a needle; and the guidewire is configured to be lockable with respect to the needle to inhibit relative motion between the guidewire and the needle; and further comprising an optical sensor located at the distal tip of the guidewire, wherein the optical sensor is configured to provide a distal field of view forward from a distal end of the needle from a lockable location of the optical sensor that is within the needle to facilitate visualization for puncturing a target with the distal end of the needle.

In Aspect 18, the subject matter of Aspect 17 optionally includes wherein the guidewire includes a first alignment feature to facilitate positioning of the optical sensor within the needle lumen at a specified offset from a distal end of the needle.

In Aspect 19, the subject matter of any one or more of Aspects 17-18 optionally include wherein the guidewire includes a light source configured to illuminate an area distal to the distal tip of the guidewire.

In Aspect 20, the subject matter of Aspect 19 optionally includes wherein the guidewire includes an optical fiber providing or in communication with the light source.

Aspect 21 is a method of visualizing during a puncture by a needle, the method comprising: locating a surface puncture site for the needle; puncturing with the needle at the surface puncture site, the needle including a guidewire received therein, wherein the guidewire includes an optical sensor within a needle lumen of the needle to provide a distal field of view forward of a distal end of the needle from a location of the optical sensor that is within the needle lumen; guiding the distal end of the needle to a target using the distal field of view forward of the distal end of the needle provided by the optical sensor; and puncturing through anatomy with the needle to arrive at the target.

In Aspect 22, the subject matter of Aspect 21 optionally includes wherein locating the surface puncture site for the needle includes imaging of a target area including the target including other than using the optical sensor.

In Aspect 23, the subject matter of any one or more of Aspects 21-22 optionally include positioning the optical sensor within the needle lumen at a specified offset from the distal end of the needle.

In Aspect 24, the subject matter of Aspect 23 optionally includes engaging an alignment feature of the guidewire with the needle to facilitate alignment of the optical sensor with the needle lumen at the specified offset.

In Aspect 25, the subject matter of any one or more of Aspects 21-24 optionally include engaging a lock with the guidewire to inhibit relative motion between the guidewire and the needle.

In Aspect 26, the subject matter of Aspect 25 optionally includes wherein engaging the lock with the guidewire includes engaging an actuator to transition the needle between a locked configuration and an unlocked configuration.

In Aspect 27, the subject matter of any one or more of Aspects 25-26 optionally include engaging the guidewire with a guidewire adaptor, wherein: the guidewire adaptor includes the lock; the guidewire adaptor is configured to engage with the needle hub to selectively couple the guidewire adaptor with the needle hub; and the lock is configured to engage with the guidewire when the guidewire adaptor is coupled with the needle hub.

In Aspect 28, the subject matter of Aspect 27 optionally includes wherein the guidewire adaptor includes an adaptor lumen, and further comprising: compressing the guidewire in the adaptor lumen to inhibit the relative motion between the guidewire and needle when the guidewire adaptor is selectively coupled with needle hub.

In Aspect 29, the subject matter of any one or more of Aspects 21-28 optionally include inserting the guidewire into a needle lumen of the needle.

In Aspect 30, the subject matter of any one or more of Aspects 21-29 optionally include coupling the guidewire with a catheter.

In Aspect 31, the subject matter of any one or more of Aspects 21-30 optionally include dilating a puncture hole provided by the needle.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A puncture visualization device for a percutaneous puncturing procedure, the puncture visualization device comprising:
   a guidewire, including:
      a proximal section;
      a distal section including a distal coil and a distal tip; and
      an inner support engaged with the distal coil;
   a needle including a needle lumen configured to receive the guidewire;
   a lock configured to engage with the guidewire to inhibit relative motion between the guidewire and the needle;
   an optical sensor, located at the distal tip of the guidewire, the optical sensor configured to be locked into a position by the lock to provide a distal field of view from a location within the needle and near a distal end of the needle for visualization to facilitate puncturing a target with the distal end of the needle; and
   wherein the guidewire includes a first alignment feature that engages with the lock so as to define a length of the guidewire within the needle that locates the optical sensor at the distal tip of the guidewire at a location that is within the needle that is at a specified offset distance from a distal end of the needle to establish the distal field of view of the optical sensor to extend beyond the distal end of the needle.

2. The puncture visualization device of claim 1, wherein the needle lumen is sized and shaped to receive the guidewire and inhibit reception of the first alignment feature.

3. The puncture visualization device of claim 1, further comprising a needle hub at a proximal end of the needle and in communication with the needle lumen of the needle.

4. The puncture visualization device of claim 3, wherein the needle hub includes:
   the lock; and
   an actuator configured to transition the puncture visualization device between a locked configuration and an unlocked configuration, wherein:
      in the locked configuration, the lock is engaged with the guidewire; and
      in the unlocked configuration, the lock is disengaged from the guidewire.

5. The puncture visualization device claim 4, wherein the lock includes an arm configured to engage with the guidewire and bias the guidewire toward a wall of the needle lumen.

6. The puncture visualization device of claim 3, further comprising a guidewire adaptor including the lock, wherein:
   the guidewire adaptor includes an adaptor lumen configured to receive the guidewire; and
   the needle hub is configured to receive the guidewire adaptor, wherein:
      the guidewire adaptor is configured to engage with the needle hub to selectively couple the guidewire adaptor with the needle hub; and
      the lock is configured to engage with the guidewire when the guidewire adaptor is coupled with the needle hub.

7. The puncture visualization device of claim 6, wherein the lock is configured to compress the guidewire in the adaptor lumen to inhibit the relative motion between the guidewire and the needle when the guidewire adaptor is selectively coupled with the needle hub.

8. The puncture visualization device of claim 1, wherein the inner support includes an inner coil.

9. The puncture visualization device of claim 8, wherein the inner coil is wound in a first direction, and the distal coil is wound in a second direction opposite the first direction.

10. The puncture visualization device of claim 8, wherein the inner coil defines an interior chamber and the optical sensor is located at least partially within the interior chamber defined by the inner coil.

11. The puncture visualization device of claim 1, wherein the distal coil has a rounded profile.

12. The puncture visualization device of claim 1, wherein the guidewire includes a light source configured to illuminate an area distal to the distal tip of the guidewire.

13. The puncture visualization device of claim 12, wherein the guidewire includes an optical fiber providing or coupled to the light source.

14. The puncture visualization device of claim 1, further comprising an electrical interconnect in communication with the optical sensor and included in the proximal section of the guidewire.

15. The puncture visualization device of claim 1, further comprising one or more of a temperature sensor or a force sensor located at the distal tip of the guidewire.

* * * * *